(12) United States Patent
Murakoshi et al.

(10) Patent No.: US 9,341,598 B2
(45) Date of Patent: May 17, 2016

(54) ULTRASONIC TESTING METHOD OF WHEEL

(75) Inventors: Hitoshi Murakoshi, Osaka (JP); Kenta Takahashi, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 226 days.

(21) Appl. No.: 14/128,649

(22) PCT Filed: Jun. 5, 2012

(86) PCT No.: PCT/JP2012/064433
§ 371 (c)(1),
(2), (4) Date: Apr. 10, 2014

(87) PCT Pub. No.: WO2012/176612
PCT Pub. Date: Dec. 27, 2012

(65) Prior Publication Data
US 2014/0224024 A1      Aug. 14, 2014

(30) Foreign Application Priority Data
Jun. 22, 2011   (JP) .................................. 2011-138534

(51) Int. Cl.
*G01N 29/04* (2006.01)
*G01N 29/24* (2006.01)
(Continued)

(52) U.S. Cl.
CPC .............. *G01N 29/04* (2013.01); *G01N 29/043* (2013.01); *G01N 29/0645* (2013.01);
(Continued)

(58) Field of Classification Search
CPC ..... G01N 29/043; G01N 29/28; G01N 29/24; G01N 29/0645; G01N 29/07; G01N 29/04; G01N 2291/044; G01N 2291/106; G01N 2291/2696; G01N 2291/2638
USPC .......................................................... 73/632
See application file for complete search history.

(56) References Cited

U.S. PATENT DOCUMENTS

| 4,566,332 A | * | 1/1986 | Collingwood | ..... G01N 29/2493 |
| | | | | 73/639 |
| 4,898,034 A | * | 2/1990 | Kupperman | ........... G01N 29/28 |
| | | | | 73/639 |

(Continued)

FOREIGN PATENT DOCUMENTS

| CN | 101639463 | * | 2/2010 |
| JP | 2003-004709 | | 1/2003 |
| JP | 2005-207811 | | 8/2005 |
| JP | 3808513 | | 5/2006 |
| JP | 2007-093311 | | 4/2007 |

OTHER PUBLICATIONS

English Translation of JP2003004709, Shigetoshi, Jan. 2003.*

*Primary Examiner* — J M Saint Surin
(74) *Attorney, Agent, or Firm* — Clark & Brody

(57) ABSTRACT

An ultrasonic testing apparatus includes an array probe 3 disposed to face a flange-side rim face 16 of a wheel 1. The ultrasonic testing apparatus also includes an array flaw detector having a function of transmitting transmission-reception control signals to the array probe, and a personal computer having a function of setting various parameters for the array flaw detector, and receiving signals from the array flaw detector so as to generate images such as an A-scope image and a B-scope image. When detecting a flaw, the array probe is disposed in such a manner that a transducer face thereof faces the flange-side rim face. At this time, an angle between the transducer alignment direction of the array probe and the radial direction of the wheel 1 is set to be 20 to 60° when viewed in the axial direction, and the flaw detection is carried out at this angle.

2 Claims, 6 Drawing Sheets

(51) Int. Cl.
  *G01N 29/28* (2006.01)
  *G01N 29/06* (2006.01)
  *G01N 29/07* (2006.01)
(52) U.S. Cl.
  CPC .............. *G01N 29/07* (2013.01); *G01N 29/24* (2013.01); *G01N 29/28* (2013.01); *G01N 2291/044* (2013.01); *G01N 2291/106* (2013.01); *G01N 2291/2638* (2013.01); *G01N 2291/2696* (2013.01)

(56) References Cited

U.S. PATENT DOCUMENTS

| | | | | |
|---|---|---|---|---|
| 5,497,662 | A | * | 3/1996 | Dykes .................. G01N 29/043 73/598 |
| 6,347,550 | B1 | * | 2/2002 | Kroening ................. B61K 9/12 73/598 |
| 2005/0022602 | A1 | * | 2/2005 | Falsetti .................. G01N 29/11 73/627 |

* cited by examiner

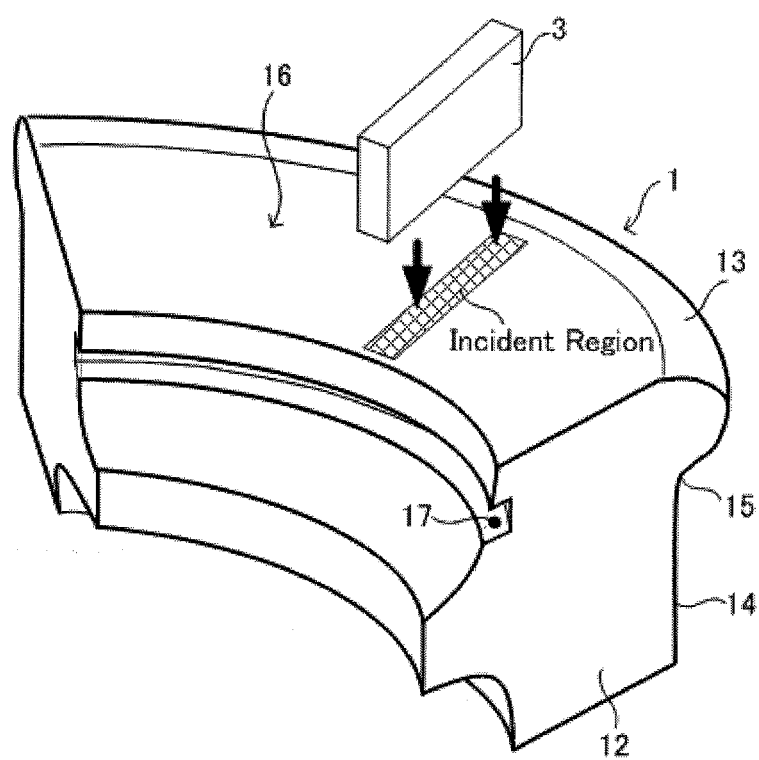

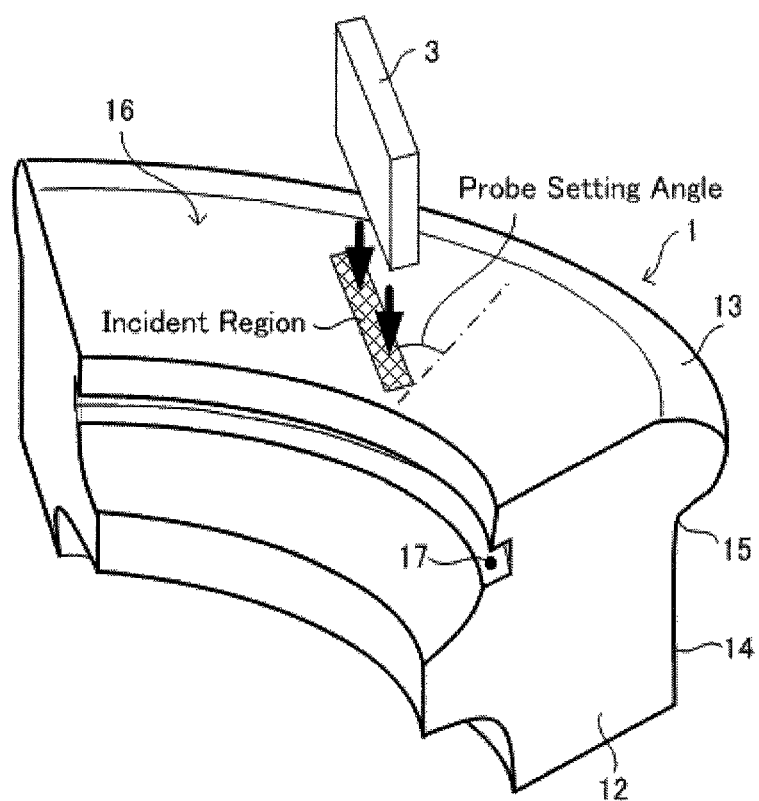

| Probe Setting Angle | Intensity of Shape Echo Compared With Intensity of Flaw Echo of Artificial Flaw | | |
|---|---|---|---|
| | Surface Texture | Ring Groove | Throat Face |
| 0° | C | C | C |
| 10° | C | C | C |
| 20° | B | B | C |
| 30° | A | A | C |
| 40° | A | A | B |
| 45° | A | A | A |

ULTRASONIC TESTING METHOD OF WHEEL

TECHNICAL FIELD

The present invention relates to an ultrasonic testing method of detecting a flaw in a rim portion by transmitting ultrasonic waves from an array probe to a flange-side rim face of a wheel. Particularly, the present invention relates to an ultrasonic testing method that reduces intensity of a shape echo of surface texture of the flange-side rim face so as to distinguish a flaw echo.

BACKGROUND ART

There has been known a conventional ultrasonic testing method that transmits ultrasonic waves from an array probe having transduces linearly arranged through a flange-side rim face of a wheel such as a railway wheel so as to detect a flaw in a rim portion of the wheel (in the rim portion, one of two side faces vertical to a shaft of the wheel, on which a flange is formed, is referred to as a "flange-side rim face" in the present specification). In this method, ultrasonic testing is carried out with the array probe opposite to the flange-side rim face while rotating the wheel in the circumferential direction. Generally, when flaw detection is carried out while rotating the wheel, an angle between the transducer alignment direction (also referred to as a "longitudinal direction", hereinafter) of the array probe and the radial direction of the wheel is set to be 0° when viewed in the axial direction so as to secure a greater area of a region where the ultrasonic waves enter the surface of the wheel (also referred to as a "incident region", hereinafter).

Unfortunately, in this ultrasonic testing, the array probe receives an echo reflected from a shape having surface texture roughness of the flange-side rim face, etc. (hereinafter referred to as a "shape echo of the surface texture"); and therefore, if a flaw exists in the vicinity of the flange-side rim face, and if intensity of the flaw echo of this flaw is equal to or less than intensity of the shape echo of the surface texture, it is difficult to detect this flaw. Hence, it has been desired to reduce the intensity of the shape echo of the surface texture of the flange-side rim face.

In the ultrasonic testing using the array probe, there has been known a method that determines an incidence angle of ultrasonic waves to an object to be detected so as to prevent shape echoes from a region other than a flaw detection region from returning to the array probe (see Patent Literature 1, for example). Unfortunately, this method cannot reduce intensity of a shape echo returning from the surface texture of the object to be detected opposite to the transducer face of the array probe.

CITATION LIST

Patent Literature

[Patent Literature 1] JP2007-93311A

SUMMARY OF INVENTION

Technical Problem

An object of the present invention, which has been made in order to solve the problems according to the conventional art, is to provide an ultrasonic testing method of detecting a flaw in a rim portion by transmitting ultrasonic waves from an array probe to a flange-side rim face of a wheel, and capable of reducing intensity of a shape echo of surface texture of the flange-side rim face, thereby distinguishing a flaw echo.

Solution to Problem

In order to solve the aforementioned problems, the present inventors have conducted various enthusiastic studies, and as a result, have obtained the following findings.

The surface texture of the flange-side rim face of the wheel includes a number of fine cutting tooth traces caused by a cutting tool at the time of machining the surface, and the cutting tooth traces are formed in a circumferential shape around a shaft of the wheel. Because the angle between the transducer alignment direction of the array probe and the radial direction of the wheel (this angle is also referred to as a "probe setting angle", hereinafter) is 0° when viewed in the axial direction, the ultrasonic waves transmitted from the array probe in the radial direction of the wheel are reflected on the cutting tooth traces vertically intersecting the radial direction of the wheel, and return to the array probe as the shape echo of the surface texture. Hence, it is difficult to distinguish a flaw echo returning from the vicinity of the flange-side rim face from a shape echo of the surface texture of the flange-side rim face (the surface texture of the flange-side rim face is also referred to simply as a "surface texture", hereinafter).

To address this difficulty, it has been studied whether or not it is feasible to distinguish the flaw echo returning from the vicinity of the flange-side rim face from the shape echo of the surface texture by tilting the probe setting angle to a degree in which no shape echo of the cutting tooth trace returns to the array probe, and a probe setting angle for attaining such a distinction has been found.

The present invention has been accomplished based on the result of the above studies by the present inventors. That is, in order to solve the aforementioned problems, the present invention provides an ultrasonic testing method of detecting a flaw in a rim portion of a wheel by transmitting ultrasonic waves from an array probe to a flange-side rim face of the wheel, the ultrasonic testing method comprising: disposing a transducer face of the array probe to face the flange-side rim face; setting an angle between a transducer alignment direction of the array probe and a radial direction of the wheel to be 20 to 60° when viewed in an axial direction of the wheel; and detecting a flaw by the array probe in which the angle is set.

According to the present invention, the angle between the transducer alignment direction of the array probe and the radial direction of the wheel when viewed in the axial direction of the wheel, that is, the probe setting angle is set to be 20° or more, and thereby allowing the shape echo of the surface texture of the flange-side rim face to hardly return to the array probe. Accordingly, the intensity of the shape echo of the surface texture is likely to become less than the intensity of the flaw echo, so that the flaw echo from the vicinity of the flange-side rim face can be more easily distinguished from the shape echo of the surface texture.

Because of the probe setting angle of 60° or less, the area of the incident region at the time of detecting a flaw while rotating the wheel becomes ½ or more of that at the probe setting angle of 0°, and the area of the incident region is not so much decreased.

Accordingly, by setting the probe setting angle to be 20 to 60°, it is possible to carry out the flaw detection with reduced intensity of the shape echo of the surface texture.

Some wheels may include ring grooves for soundproofing. The ring groove is formed in the outward radial direction from an inner face of the rim portion around its entire circumference.

In such a wheel, if the probe setting angle is 0°, the ultrasonic waves transmitted in the inward radial direction of the wheel are reflected on the ring groove vertically intersecting the radial direction of the wheel, and likely to return to the array probe; and therefore, it is difficult to distinguish the flaw echo returning from the vicinity of the ring groove from the shape echo of the ring groove.

It was found that at the probe setting angle of 20 to 60°, the shape echo of the ring groove hardly returns to the array probe, and thus the intensity of the shape echo of the ring groove is likely to become less than that of the flaw echo. Hence, it becomes easier to distinguish the flaw echo returning from the vicinity of the ring groove from the shape echo of the ring groove.

Accordingly, in order to detect a flaw existing in two different regions in the vicinity of the surface texture and in the vicinity of the ring groove, this flaw can be accurately detected with a single array probe by simply setting the probe setting angle to be 20 to 60°, which reduces the intensities of the shape echoes of the surface texture and of the ring groove.

At the probe setting angle of 0°, a shape echo of a throat face located between the surface of the flange portion and a wheel tread (face of the rim portion to be in contact with a rail) is likely to return to the array probe; and therefore, it is difficult to distinguish the flaw echo returning from the vicinity of the throat face from the shape echo of the throat face. To address this difficulty, it has been studied whether or not it is feasible to distinguish the flaw echo returning from the vicinity of the throat face from the shape echo of the throat face by tilting the probe setting angle to a degree in which no shape echo of the throat face returns to the array probe, and as a result, it was found that the probe setting angle is preferably set to be 40 to 60°.

In the wheel having no ring groove, in order to detect a flaw existing in two different regions in the vicinity of the flange-side rim face and in the vicinity of the throat face, this flaw can be accurately detected with a single array probe by simply setting the probe setting angle to be 40 to 60° which reduces the intensities of the shape echoes of the surface texture of the flange-side rim face and of the throat face.

In the wheel having the ring groove, in order to detect a flaw existing in three different regions in the vicinity of the flange-side rim face, in the vicinity of the ring groove, and in the vicinity of the throat face, this flaw can be accurately detected with a single array probe by simply setting the probe setting angle to be 40 to 60°, which reduces the intensities of the shape echoes of the surface texture of the flange-side rim face, of the ring groove, and of the throat face, respectively.

Advantageous Effect of Invention

According to the present invention, in the ultrasonic testing method of detecting a flaw in the rim portion by transmitting ultrasonic waves from the array probe to the flange-side rim face of the wheel, it is possible to reduce intensity of the shape echo of the surface texture of the flange-side rim face, and thereby distinguishing the flaw echo.

BRIEF DESCRIPTION OF DRAWINGS

FIG. 2A is a schematic drawing of the ultrasonic testing apparatus, and

FIG. 2B is a schematic drawing of an array probe included in the ultrasonic testing apparatus.

FIG. 3 is a perspective view showing an arrangement position of the array probe in a conventional ultrasonic testing method.

FIG. 4A is a photograph of the B-scope, and FIG. 4B is a schematic drawing of the B-scope.

FIG. 5A is a cross sectional drawing in a radial direction of the propagation paths when viewed in a circumferential direction of the wheel, and FIG. 5B is a plan view of the propagation paths when viewed in an axial direction of the wheel.

FIG. 6 is a perspective view showing an arrangement position of the array probe in the ultrasonic testing method according to the embodiment of the present invention.

DESCRIPTION OF EMBODIMENT

Hereinafter, an ultrasonic testing method according to an embodiment of the present invention will be described with reference to accompanying drawings. In the ultrasonic testing method according to the present embodiment, a flaw in a rim portion is detected by transmitting ultrasonic waves onto a flange-side rim face of a wheel.

Figure 1:
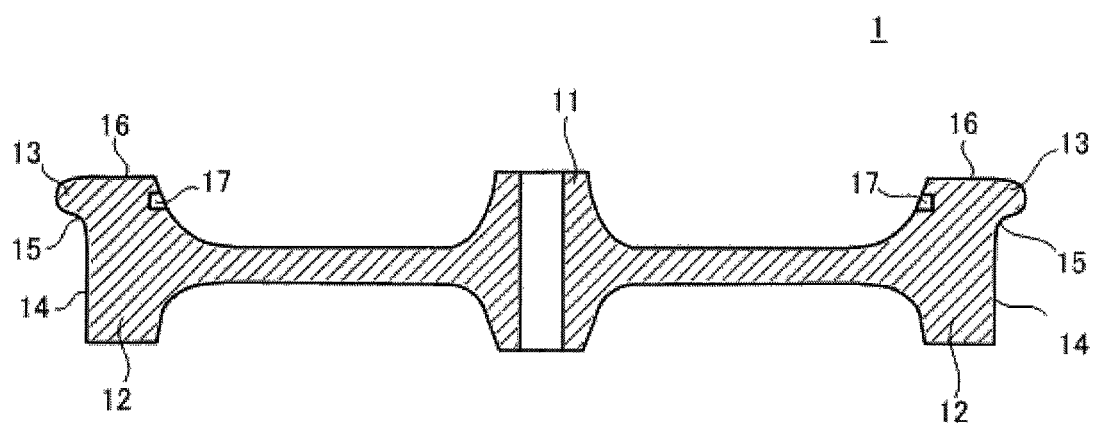
FIG. 1 is a cross sectional drawing in a radial direction of a wheel showing an example of the wheel to which an ultrasonic testing method according to an embodiment of the present invention is applied.

FIG. 1 is a cross sectional drawing in a radial direction of a wheel showing an example of the wheel to which an ultrasonic testing method according to the present embodiment is applied.

A wheel 1 is a railway wheel, and includes a boss 11 at its center, and a rim portion 12 at the circumference of the wheel. The rim portion 12 includes a flange portion 13 projecting in the outer circumferential direction and a wheel tread 14 to be in contact with a rail, both of which extend around the entire outer circumference of the wheel. In the present specification, a portion located between the surface of the flange portion 13 and the wheel tread 14 is referred to as a throat face 15. In the rim portion 12, one of two side faces vertical to a shaft of the wheel 1, on which the flange portion 13 is formed, is referred to as a flange-side rim face 16.

The wheel 1 may include a ring groove 17 for soundproofing, and may include no ring groove 17 in some cases, and FIG. 1 shows the wheel 1 including the ring groove 17 as an example of the wheel 1. The ring groove 17 is formed in the outward radial direction from the inner face of the rim portion 12 around the entire circumference.

Figure 2A:
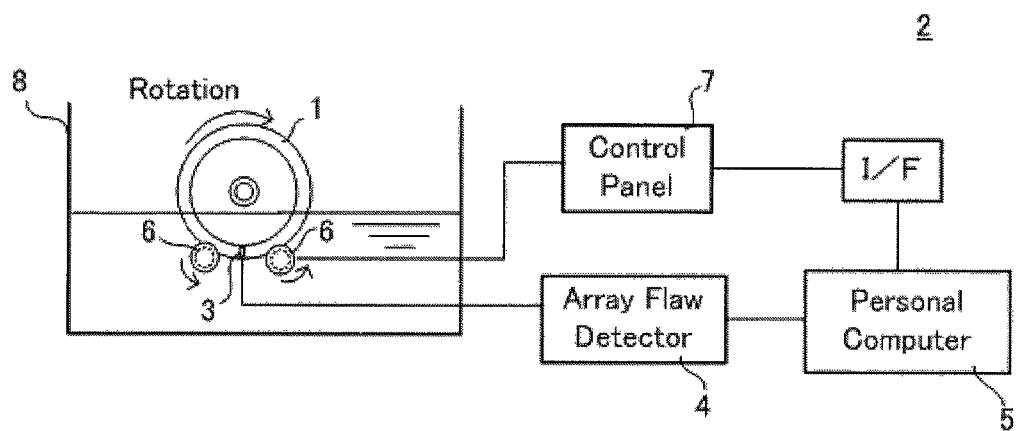
FIGS. 2A and 2B are drawings explaining an example of an ultrasonic testing apparatus used in the ultrasonic testing method.
Figure 2B:
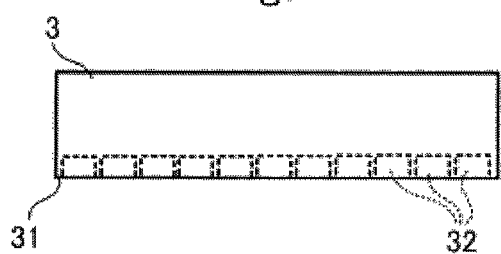

FIGS. 2A and 2B are drawings explaining an example of an ultrasonic testing apparatus used in the ultrasonic testing method according to the present embodiment; FIG. 2A is a schematic drawing of the ultrasonic testing apparatus, and FIG. 2B is a schematic drawing of an array probe included in the ultrasonic testing apparatus.

The ultrasonic testing apparatus 2 includes the array probe 3 disposed to face the flange-side rim face 16 of the wheel 1. The ultrasonic testing apparatus 2 also includes an array flaw detector 4 having a function of transmitting transmission-reception control signals to the array probe 3 etc., and also amplifying signals received from the array probe 3, a personal computer 5 having a function of setting various parameters for the array flaw detector 4, and receiving signals from the array flaw detector 4 so as to generate images such as an A-scope image and a B-scope image, etc., and a control panel 7 for supplying rotation signals and others to a rotary driving section 6 described below.

The ultrasonic testing apparatus 2 further includes the rotary driving section 6 for supporting a bottom of the wheel 1 with its shaft horizontal, and also rotating the wheel 1 for the purpose of detecting flaws in the entire circumference of the rim portion 12, and a tank 8 for soaking the wheel 1 and the array probe 3 in water. The array probe 3 includes multiple transducers 32 linearly arranged, and a face of the array probe 3 where ultrasonic waves are transmitted from the transducers 32 is referred to as a transducer face 31.

An example of the ultrasonic testing method using the aforementioned ultrasonic testing apparatus 2 will be described, hereinafter.

In order to carry out the ultrasonic testing, the transducer face 31 of the array probe 3 is disposed to face the flange-side rim face 16, the tank 8 is filled with water as a coupling medium so that the wheel 1 and the array probe 3 are soaked in the water. Oil or the like may also be used as the coupling medium. Flaw detecting conditions, such as intensity of the ultrasonic waves transmitted from the array probe 3 and scanning speed, etc., are set in the personal computer 5, and the flaw detecting conditions are converted into the transmission-reception control signals by the array flaw detector 4, and then transmitted to the array probe 3. The array probe 3 transmits the ultrasonic waves through the flange-side rim face 16 into the rim portion 12, and transmits signals corresponding to echo signals received from the rim portion 12 to the array flaw detector 4. The array flaw detector 4 amplifies the received signals from the array probe 3, and then transmits the signals to the personal computer 5, and the personal computer 5 displays images such as an A-scope image and a B-scope image. The personal computer 5 transmits rotation signals to the rotary driving section 6 via the control panel 7 so as to rotate the wheel 1. In this manner, the flaw detection in the rim portion 12 is carried out in the circumferential direction.

The transmission and reception of the ultrasonic waves from the array probe 3 are carried out, for example, by linear scanning (in the linear scanning, a certain number of the transducers 32 included in the array probe 3 are defined as a single transmission unit, and in transmission of the ultrasonic waves per transmission unit, the ultrasonic wave from each transducer 32 is transmitted in parallel with each other, or each transducer 32 transmits the ultrasonic wave at different timing so as to concentrate the ultrasonic wave transmitted from each transducer 32 at one point. In this state, the array probe 3 is controlled by the transmission-reception control signals from the array flaw detector 4 such that the transmission unit sequentially shifts in the alignment direction of the transducers 32, and thereby performing parallel scanning with the ultrasonic waves); or by steering scanning (in the steering scanning, a certain number of the transducers 32 included in the array probe 3 are defined as a single transmission unit, and in transmission of the ultrasonic waves per transmission unit, the ultrasonic wave from each transducer 32 is transmitted in parallel with each other, or the ultrasonic wave is transmitted from each transducer 32 at different timing so as to concentrate the ultrasonic wave transmitted from each transducer 32 at one point. In this state, the exit angle is varied, and thereby performing the scanning).

The ultrasonic testing method according to the present invention has a feature in the arrangement position of the array probe 3, and thus the arrangement position of the array probe 3 will be described below. Conventionally, in general, for the purpose of securing a greater area where the incident region passes at the time of detecting a flaw while the wheel is being rotated, the angle (probe setting angle) between the transducer alignment direction (longitudinal direction) of the array probe 3 and the radial direction of the wheel is set to be 0° when viewed in the axial direction.

FIG. 3 is a perspective view showing an arrangement position of the array probe in a conventional ultrasonic testing method.

FIG. 3 shows only a part of the wheel 1.

The incident region extends in the radial direction.

Figure 4A:
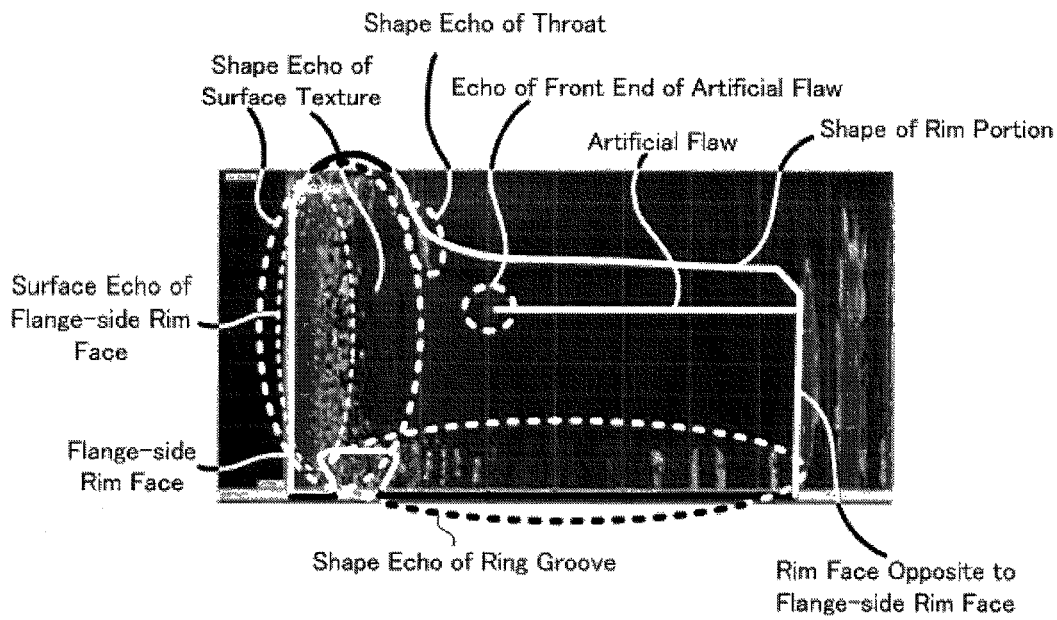
FIGS. 4A and 4B show a B-scope in flaw detection at a probe setting angle of 0°.
Figure 4B:
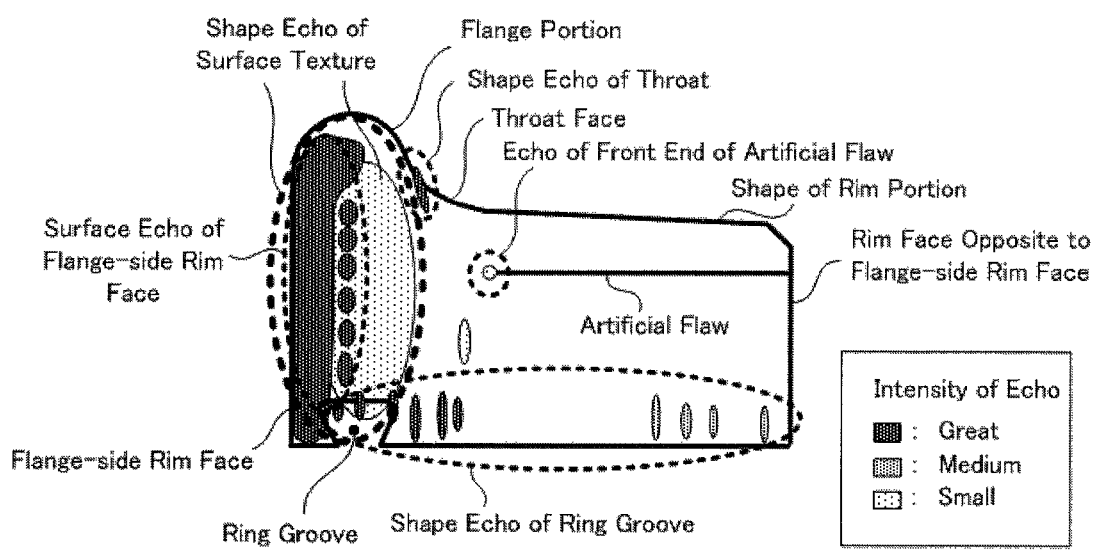

FIGS. 4A and 4B show a B-scope in flaw detection at a probe setting angle of 0°; FIG. 4A is a photograph of the B-scope, and FIG. 4B is a schematic drawing of the B-scope. In both the figures, the lateral axis represents the propagation time of the ultrasonic wave, and the vertical axis represents the scanning position of the ultrasonic wave. Specifically, the lateral axis indicates a depth position from the flange-side rim face 16, and the vertical axis indicates a position in the radial direction in the flange-side rim face 16. In FIG. 4, the shape of the rim portion is indicated by solid lines.

In the rim portion 12 imaged by this B-scope, such an artificial flaw of a flat-bottomed hole of 1 mm φ is formed that vertically extends from a rim face opposite to the flange-side rim face 16 toward the flange-side rim face 16. A distance from the flange-side rim face 16 to a front end of the artificial flaw is 50 mm, and an echo of the front end of the artificial flaw (flaw echo) is detected by the B-scope.

In the B-scope, a surface echo of the flange-side rim face 16 appears in the vicinity of the flange-side rim face 16. The shape echo of the surface texture appears in a region from the flange-side rim face 16 to a portion deeper than the surface echo. If the front end of the artificial flaw is formed in a region where this shape echo of the surface texture appears, and if the intensity of the flaw echo of this artificial flaw is equal to or less than the intensity of the shape echo of the surface texture, it is difficult to detect this artificial flaw.

A shape echo of the ring groove 17 appears at a position of the ring groove 17, and also at a position deeper than the ring groove 17, and a shape echo of the throat face 15 appears in the vicinity of the throat face 15. If the artificial flaw is formed in regions where the shape echoes of the ring groove 17 and of the throat face 15 appear, and if the intensity of the flaw echo of this artificial flaw is equal to or less than each intensity of the shape echoes of the ring groove 17 and of the throat face 15, it is difficult to detect this artificial flaw.

Figure 5A:
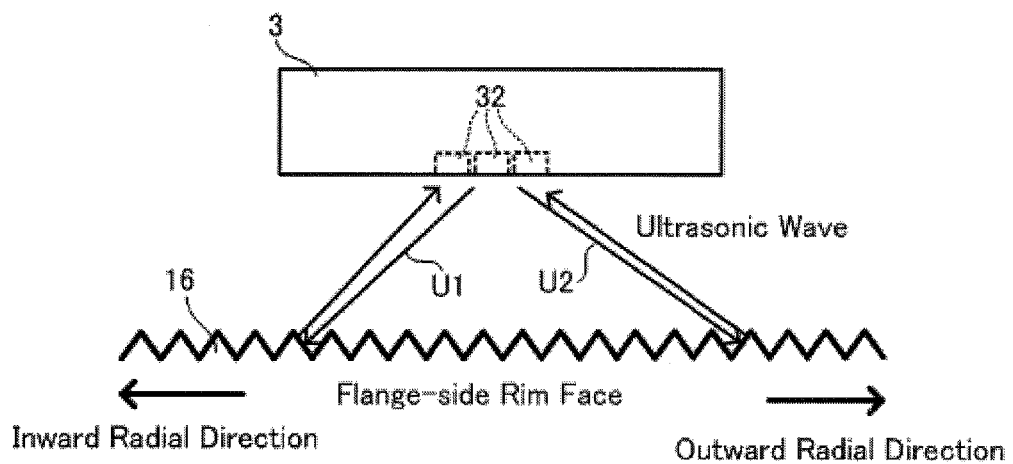
FIGS. 5A and 5B are drawings showing propagation paths of ultrasonic waves transmitted to a flange-side rim face.
Figure 5B:
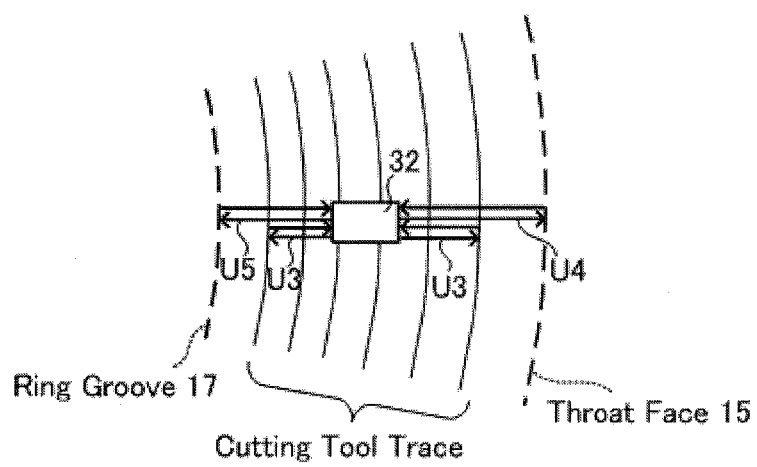

FIGS. 5A and 5B are drawings showing propagation paths of ultrasonic waves transmitted to the flange-side rim face 16; FIG. 5A is a cross sectional drawing in a radial direction of the propagation paths when viewed in a circumferential direction of the wheel 1, and FIG. 5B is a plan view of the propagation paths when viewed in an axial direction of the wheel 1.

Each propagation path viewed in the circumferential direction of the wheel 1 will be described with reference to FIG. 5A.

The surface texture of the flange-side rim face 16 of the wheel includes a number of fine cutting tooth traces generated by a cutting tool at the time of machining the surface, and the cutting tooth traces are formed in a circumferential shape around the shaft of the wheel.

Ultrasonic waves U1 obliquely transmitted from the transducers 32 across the flange-side rim face 16 in the inward radial direction are reflected in the inward radial direction if the flange-side rim face 16 is flat. The flange-side rim face 16, however, has a number of fine rough cutting tooth traces in the radial direction. Hence, part of the ultrasonic waves is reflected on the flange-side rim face 16, and returns to the transducers 32 when viewed in the circumferential direction of the wheel 1. Part of ultrasonic waves U2 that is obliquely transmitted from the transducers 32 across the flange-side rim face 16 in the outward radial direction is also reflected on the flange-side rim face 16, and returns to the transducers 32 when viewed in the circumferential direction of the wheel 1.

Each propagation path viewed in the axial direction of the wheel 1 will be described with reference to FIG. 5B. In FIG. 5B, only several cutting tool traces are shown as a matter of convenience.

Because of the probe setting angle of 0°, ultrasonic waves U3 from the transducers 32 are vertically reflected on the cutting tool traces, and return to the transducers 32. If the flange-side rim face 16 has a rough surface in the circumferential direction, the ultrasonic waves are dispersedly reflected on the flange-side rim face 16 in the circumferential direction; but the flange-side rim face 16 includes the cutting tool traces that make the surface smooth in the circumferential direction, which are generated by the cutting tool at the time of machining the surface, and thus many of the ultrasonic waves return to the transducers 32 when viewed in the axial direction of the wheel 1.

As described above, part of the ultrasonic waves transmitted from the array probe 3 returns to the array probe 3 when viewed in both the circumferential direction and the axial direction of the wheel 1. Consequently, part of the ultrasonic waves transmitted from the array probe 3 is reflected on the surface texture, and returns to the array probe 3, which appears in the B scope as the shape echo of the surface texture.

Such a shape echo of the surface texture that returns to the array probe 3 is not resulted from an echo of the ultrasonic waves transmitted and received in the approximately vertical direction, but resulted from an echo of the ultrasonic waves obliquely transmitted and received across the flange-side rim face 16 by the transducers 32, and thus this echo has a longer propagation time than that of the surface echo of the flange-side rim face 16 (the surface echo of the flange-side rim face 16 is formed by ultrasonic waves transmitted and received in the approximately vertical direction across the flange-side rim face 16). Hence, in the B-scope, the shape echo of the surface texture appears even at a deeper position than the surface echo of the flange-side rim face 16. Consequently, it is difficult to detect a flaw existing at a position where the shape echo of the surface texture appears in the B-scope.

Because of the probe setting angle of 0°, ultrasonic waves U4 and U5 from the transducers 32 are vertically reflected on the throat face 15 and on the ring groove 17, respectively, and return to the transducers 32. Hence, the shape echoes of the throat face 15 and the ring groove 17 appear in the B scope. Consequently, it is difficult to detect a flaw existing at positions where the shape echoes of the throat face 15 and of the ring groove 17 appear in the B-scope.

In the present embodiment, the ultrasonic testing is carried out using the probe setting angle of more than 0°.

Figures 7, 8:
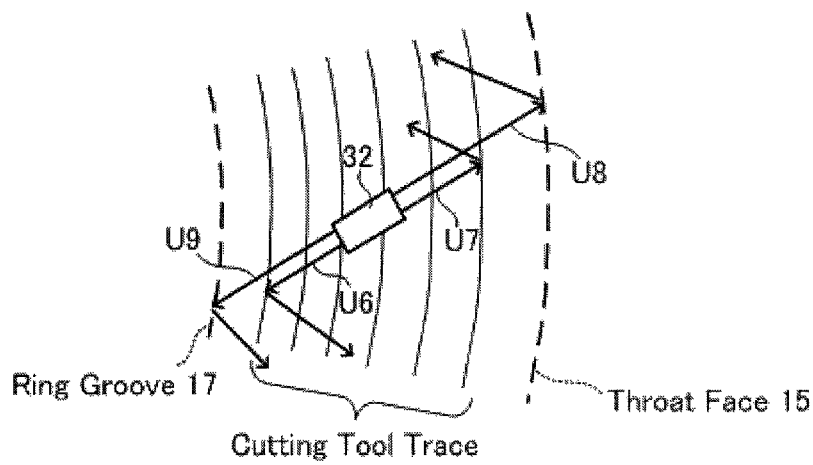
FIG. 7 is a plane view of the propagation paths of ultrasonic waves when viewed in the axial direction of the wheel.
FIG. 8 is a drawing showing comparison of each intensity of shape echoes of a surface texture, of a ring groove, and of a throat face with intensity of a flaw echo of an artificial flaw formed in a rim portion, using various probe setting angles.

FIG. 6 is a perspective view showing an arrangement position of the array probe. Only part of the wheel 1 is shown. The incident region is oblique relative to the radial direction. FIG. 7 is a plane view of the propagation paths of ultrasonic waves when viewed in the axial direction of the wheel 1.

In the case of the probe setting angle of more than 0°, the propagation path of the ultrasonic waves viewed in the circumferential direction of the wheel 1 is the same as that at the probe setting angle of 0°, and as similar to the case described with reference to FIG. 5A, part of the ultrasonic waves transmitted from the transducers 32 in the inward and outward radial directions is reflected on the flange-side rim face 16, and returns to the transducers 32.

In the propagation path of the ultrasonic waves viewed in the axial direction of the wheel 1, since the probe setting angle is more than 0° as shown in FIG. 7, ultrasonic waves U6 transmitted from the transducers 32 in the inward radial direction are reflected on the cutting tool traces, and thereafter hardly return to the transducers 32. Ultrasonic waves U7 transmitted from the transducers 32 in the outward radial direction are reflected on the cutting tool traces, and thereafter hardly return to the transducers 32, either.

Because of the probe setting angle of more than 0°, ultrasonic waves U8 transmitted from the transducers 32 to the throat face 15 are reflected on the throat face 15, and thereafter hardly return to the transducers 32. Similarly, ultrasonic waves U9 transmitted from the transducers 32 to the ring groove 17 are reflected on the ring groove 17, and thereafter hardly return to the transducers 32.

FIG. 8 is a drawing showing comparison of each intensity of shape echoes of a surface texture, of the ring groove 17, and of the throat face 15 with intensity of a flaw echo of an artificial flaw formed in the rim portion 12, using various probe setting angles.

Each of the array probes 3 that were used had 128 transducers, a pitch between the adjacent transducers of 1 mm, the simultaneous excitation number of 24, and an array probe length of 128 mm. The array probes had four different widths of 7 mm, 9 mm, 11 mm, and 12.5 mm.

As similar to the B scope shown in FIG. 4, an artificial flaw of a flat-bottomed hole of 1 mm $\phi$ vertically extending from the rim face opposite to the flange-side rim face 16 toward the flange-side rim face 16 was formed such that a distance from the front end of the artificial flaw to the flange-side rim face 16 was 50 mm.

Sensitivity of the transducers 32 was adjusted such that the intensity of the flaw echo of the artificial flaw becomes the same at every probe setting angle.

As shown in FIG. 8, with respect to the surface texture of the flange-side rim face 16, the ring groove 17, and the throat face 15, each case of having the intensity of the shape echo sufficiently less than the intensity of the flaw echo of the artificial flaw was indicated by a reference character A; each case of having the intensity of the shape echo less than the intensity of the flaw echo of the artificial flaw, in which there was a small difference in intensity but the artificial flaw could be distinguished, was indicated by a reference character B; and each case of having the intensity of the shape echo equal to or more than the intensity of the flaw echo of the artificial flaw was indicated by a reference character C.

In order to reduce each intensity of the shape echoes of the surface texture of the flange-side rim face 16, of the ring groove 17, and of the throat face 15 to be less than the intensity of the flaw echo of the artificial flaw, the probe setting angle may be set as follows. Although four types of the array probes 3 having different widths were used, but all the array probes 3 had the same result.

In order to reduce the intensity of the shape echo of the surface texture to be less than the intensity of the flaw echo of the artificial flaw, the probe setting angle is preferably 20 to 45°, and more preferably 30 to 45°.

In order to reduce the intensity of the shape echo of the ring groove 17 to be less than the intensity of the flaw echo of the artificial flaw, the probe setting angle is preferably 20 to 45°, and more preferably 30 to 45°.

In order to reduce the intensity of the shape echo of the throat face 15 to be less than the intensity of the flaw echo of the artificial flaw, the probe setting angle is preferably 40 to 45°, and more preferably 45°.

Although the result using the probe setting angle of more than 45° is not shown in FIG. 8, at the probe setting angle of more than 45° to less than 90°, each intensity of the shape echoes of the surface texture, the ring groove 17, and the throat face 15 was sufficiently less than the intensity of the flaw echo of the artificial flaw.

As the probe setting angle becomes greater, the area where the incident region passes becomes smaller at the time of detecting a flaw while the wheel is being rotated. Accordingly, the probe setting angle is set to be 60° or less so as to secure the area where the incident region passes to be ½ or more of the area using the probe setting angle of 0°. If it is acceptable to have a smaller area where the incident region passes, the probe setting angle may be 70° or less, or 80° or less.

Accordingly, the probe setting angle is set to be 20 to 60° in order to carry out the ultrasonic testing with the reduced intensity of the shape echo of the surface texture of the flange-side rim face 16. More preferably, the probe setting angle is set to be 30 to 60°. Through this configuration, the shape echo of the surface texture hardly returns to the array probe. Accordingly, the intensity of the shape echo of the surface texture becomes less than that of the flaw echo of the artificial flaw, which makes it easier to distinguish the flaw echo returning from the vicinity of the flange-side rim face 16 from the shape echo of the surface texture.

In the case of the wheel 1 having the ring groove 17, the probe setting angle is set to be 20 to 60°. Preferably, the probe setting angle is set to be 30 to 60°. Through this configuration, the intensity of the shape echo of the ring groove 17 becomes less than that of the flaw echo from the artificial flaw. Hence, it becomes easier to distinguish the flaw echo returning from the vicinity of the ring groove 17 from the shape echo of the ring groove 17.

Accordingly, in detecting a flaw existing in two different regions in the vicinity of the surface texture and in the vicinity of the ring groove 17, this flaw can be accurately detected with a single array probe by simply setting the probe setting angle to be 20 to 60°, which reduces the intensities of the shape echoes of the surface texture and of the ring groove 17.

In order to carry out the ultrasonic testing with the reduced intensity of the shape echo of the throat face 15, the probe setting angle is set to be 40 to 60°. More preferably, the probe setting angle is set to be 45 to 60°. Through this configuration, the intensity of the shape echo of the throat face 15 becomes less than that of the flaw echo from the artificial flaw. Accordingly, it becomes easier to distinguish the flaw echo returning from the vicinity of the throat face 15 from the shape echo of the throat face 15.

Accordingly, in the wheel having no ring groove 17, in detecting a flaw existing in two different regions in the vicinity of the flange-side rim face 16 and in the vicinity of the throat face 15, this flaw can be accurately detected with a single array probe by simply setting the probe setting angle to be 40 to 60°, which reduces the intensities of the shape echoes of the surface texture and of the throat face 15.

In the wheel having the ring groove 17, in detecting a flaw existing in three different regions in the vicinity of the flange-side rim face 16, in the vicinity of the ring groove 17, and in the vicinity of the throat face 15, this flaw can be accurately detected with a single array probe by simply setting the probe setting angle to be 40 to 60°, which reduces the intensities of the shape echoes of the surface texture of the flange-side rim face 16, of the ring groove 17, and of the throat face 15, respectively.

The present invention is not limited to the configuration of the above embodiment, and various modifications can be made without departing from the spirit and scope of the present invention.

REFERENCE SIGNS LIST

1 . . . Wheel
16 . . . Flange-side rim face
3 . . . Array probe
31 . . . Transducer face

The invention claimed is:

1. An ultrasonic testing method of detecting a flaw in a rim portion of a wheel by transmitting ultrasonic waves from an array probe to a flange-side rim face of the wheel, the ultrasonic testing method comprising:
    disposing a transducer face of the array probe to face the flange-side rim face;
    setting an angle between a transducer alignment direction of the array probe and a radial direction of the wheel to be 20 to 60° when viewed in an axial direction of the wheel, the array probe having two end parts in the transducer alignment direction, the radial direction passing through one of the two end parts of the array probe, the one end part of the array probe being closer to a shaft of the wheel; and
    detecting the flaw by the array probe in which the angle is set.

2. The ultrasonic testing method according to claim 1, wherein the angle is set to be 40 to 60°.

* * * * *